United States Patent
Boettcher et al.

(10) Patent No.: US 7,084,143 B2
(45) Date of Patent: Aug. 1, 2006

(54) N-(INDOLECARBONYL) PIPERAZINE DERIVATIVES

(75) Inventors: Henning Boettcher, Darmstadt (DE); Christoph Seyfried, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/013,908

(22) Filed: Dec. 17, 2004

(65) Prior Publication Data
US 2005/0096330 A1  May 5, 2005

Related U.S. Application Data

(63) Continuation of application No. 10/031,367, filed as application No. PCT/EP00/06464 on Jul. 7, 2000, now Pat. No. 6,838,461.

(30) Foreign Application Priority Data
Jul. 22, 1999 (DE) ................. 199 34 433

(51) Int. Cl.
A61K 31/497 (2006.01)
C07D 403/06 (2006.01)
(52) U.S. Cl. ................ 514/254.09; 544/373
(58) Field of Classification Search ............ 544/373; 514/254.09
See application file for complete search history.

(56) References Cited

U.S. PATENT DOCUMENTS
6,218,394 B1   4/2001   Perregaard et al.

FOREIGN PATENT DOCUMENTS

| EP | 0 559 240 | 6/1994 |
|---|---|---|
| EP | 03 209 83 | 6/1995 |
| HU | P9603371 | 9/1997 |
| WO | WO 99 11 641 | 3/1999 |

OTHER PUBLICATIONS

Robichaud et al., Annual Reports in Medicinal Chemistry, vol. 35, pp. 11-20 (2000).
Written Opinion in corresponding PCT application which cites EP 599,240, 1994.

*Primary Examiner*—Peter O'Sullivan
(74) *Attorney, Agent, or Firm*—Millen, White, Zelano, Branigan, P.C.

(57) ABSTRACT

The invention relates to compounds of formula (I) wherein $R^1$, $R^2$, $R^4$ and $R^5$ have the meaning given in Claim 1. Said compounds are potent $5-HT_{2A}$-antagonists and are suitable for the treatment of psychosis, schizophrenia, depression, neurological disorders, memory disorders, Parkinson's disease, amytrophic lateral sclerosis, Alzheimer's disease, Huntington's disease, eating disorders, e.g. nervous bulimia and anorexia and premenstrual syndrome and/or for positively influencing compulsive behaviors (obsessive-compulsive disorder, OCD).

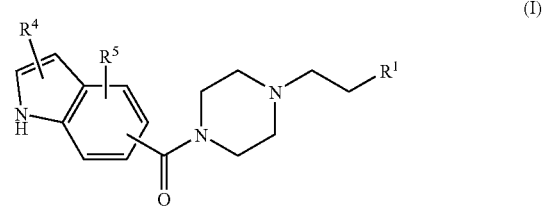

(I)

27 Claims, No Drawings

N-(INDOLECARBONYL) PIPERAZINE DERIVATIVES

This application is a continuation of copending application Ser. No. 10/031.367 filed Jun. 3, 2002, now U.S. Pat. No. 6,838,461, which is the national phase application under 35 USC §371 (c)(1) of International Patent Application No. PCT/EP00/06464 filed Jul. 7, 2000.

The invention relates to compounds of the formula I

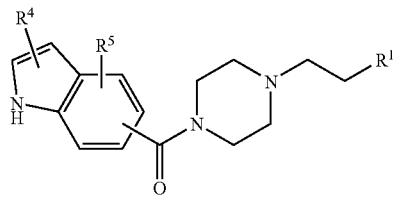

in which
- $R^1$ is a phenyl or naphthyl radical which is unsubstituted or substituted by $R^2$ and/or $R^3$ or is $Het^1$,
- $R^2$, $R^3$ in each case independently of one another are Hal, A, OA, OH or CN,
- $R^4$, $R^5$ in each case independently of one another are H, CN, acyl, Hal, A, OA, OH, $CONH_2$, CONHA or $CONA_2$,
- $R^4$ and $R^5$ together are also alkylene having 3–5 C atoms,
- $Het^1$ is a mono- or binuclear unsaturated hetero-cyclic ring system, which is unsubstituted or mono- or disubstituted by Hal, A, OA or OH and contains one, two or three identical or different heteroatoms such as nitrogen, oxygen and sulfur,
- A is alkyl having 1–5 C atoms,
- Hal is F, Cl, Br or I, and where the indole ring can also be replaced by an isatin unit, and their physiologically acceptable salts and solvates, (1H-indol-5-yl)-(4-phenethylpiperazin-1-yl)methanone being excluded.

The invention was based on the object of finding novel compounds having valuable properties, in particular those which can be used for the production of medicaments.

It has been found that the compounds of the formula I and their physiologically acceptable salts and solvates have valuable pharmacological properties together with good tolerability, as they have actions on the central nervous system. The compounds have a strong affinity for 5-$HT_{2A}$ receptors; they furthermore exhibit 5-$HT_{2A}$ receptor-antagonistic properties.

For the in-vitro detection of the affinity for 5-$HT_{2A}$ receptors, it is possible to use, for example, the following test (Example A1). The 5-$HT_{2A}$ receptors are exposed to both [$^3$H]ketanserin (a substance known for its affinity for the receptor) and the test compound. The decrease in the affinity of [$^3$H]ketanserin for the receptor is a sign of the affinity of the test substance for the 5-$HT_{2A}$ receptor. Detection is carried out analogously to the description of J. E. Leysen et al., Molecular Pharmacology, 1982, 21: 301–314 or as also described, for example, in EP 0320983.

The efficacy of the compounds according to the invention as 5-$HT_{2A}$ receptor antagonists can be measured in vitro analogously to W. Feniuk et al., Mechanisms of 5-hydroxytryptamine-induced vasoconstriction, in: The Peripheral Actions of 5-Hydroxytryptamine, ed. Fozard JR, Oxford University Press, New York, 1989, p. 110. Thus the contractility of the rat tail artery, caused by 5-hydroxytryptamine, is mediated by 5-$HT_{2A}$ receptors. For the test system, vessel rings, prepared from the ventral rat tail artery, are subjected to perfusion with an oxygen-saturated solution in an organ bath. By introduction of increasing concentrations of 5-hydroxytryptamine into the solution, a response to the cumulative concentration of 5-HT is obtained. The test compound is then added to the organ bath in suitable concentrations and a second concentration curve is measured for 5-HT. The strength of the test compound on the shift of the 5-HT-induced concentration curve to higher 5-HT concentrations is a measure of the 5-$HT_{2A}$ receptor-antagonistic property in vitro.

The 5-$HT_{2A}$-antagonistic property can be determined in vivo analogously to M. D. Serdar et al., Psychopharmacology, 1996, 128: 198–205.

Other compounds which likewise exhibit 5-$HT_2$-antagonistic actions are described, for example, in EP 0320983.

Similar piperazine derivatives having antiarrhythmic properties are disclosed, for example, in EP 0431945. Other indolecarbonyl derivatives having analgesic properties are described in EP 0599240. WO 99/11641 describes phenylindole derivatives having 5-$HT_2$-antagonistic properties.

The compounds of the formula I are therefore suitable both in veterinary and in human medicine for the treatment of functional disorders of the central nervous system and also of inflammation. They can be used for the prophylaxis and for the control of the sequelae of cerebral infarcts (cerebral apoplexy) such as stroke and cerebral ischaemia and for the treatment of extrapyramidal motor side effects of neuroleptics and also of Parkinson's disease, for the acute and symptomatic therapy of Alzheimer's disease and the treatment of amyotrophic lateral sclerosis. They are likewise suitable as therapeutics for the treatment of brain and spinal cord traumata. In particular, however, they are suitable as pharmaceutical active compounds for anxiolytics, antidepressants, antipsychotics, neuroleptics, antihypertensives and/or for positively affecting compulsive behaviour (obsessive-compulsive disorder, OCD; e.g. WO 9524194), anxiety states and physiological changes which accompany anxiety states such as, for example, tachycardia, tremors or sweating (e.g. EP 319962), panic attacks, psychoses, schizophrenia, anorexia, delusional obsessions, agoraphobia, migraine, Alzheimer's disease, sleep disorders and also sleep apnoea, tardive dyskinesias, learning disorders, age-dependent memory disorders, eating disorders such as bulimia, drug abuse such as, for example, abuse of alcohol, opiates, nicotine, psychostimulants such as, for example, cocaine or amphetamines (e.g. U.S. Pat. No. 6004980), sexual functional disorders, painful conditions of all kinds and fibromyalgia (e.g. WO 9946245).

The compounds of the formula (I) are suitable for the treatment of extrapyramidal side effects (EPS) in neuroleptic drug therapy. EPS is characterized by Parkinson-like syndromes, akathisia and dystonic reactions (e.g. EP 337136). They are further suitable for the treatment of nervous anorexia, angina, Reynaud's phenomenon, coronary vasospasms, in the prophylaxis of migraine (e.g. EP 208235), pain and neuralgia (e.g. EP 320983), for the treatment of the Rett syndrome with autistic traits, of the Asperger syndrome, of autism and autistic disorders, in concentration deficiencies, developmental disorders, hyperactivity states with mental underdevelopment and stereotypic behavioural states (e.g. WO 9524194).

In addition, they are suitable for the treatment of endocrine disorders such as hyperprolactinaemia, furthermore in vasospasms, thrombotic disorders (e.g. WO 9946245) hypertension and gastrointestinal disorders.

They are furthermore suitable for the treatment of cardiovascular disorders and also extrapyramidal symptoms such as described in WO 99/11641 on page 2, lines 24–30.

The compounds according to the invention are further suitable for decreasing intraocular pressure and for the treatment of glaucoma. They are also suitable in animals for the prophylaxis and treatment of symptoms of intoxication on the administration of ergovaline. The compounds are furthermore suitable for the treatment of disorders of the cardiovascular system (WO 99/11641, page 3, lines 14–15).

The compounds according to the invention can also be employed together with other active compounds in the treatment of schizophrenia. Possible other active compounds are the compounds mentioned in WO 99/11641 on page 13, lines 20–26.

They can furthermore be employed as intermediates for the production of further pharmaceutical active compounds.

The invention relates to the N-(indolecarbonyl)-piperazine derivatives of the formula I and to their physiologically acceptable acid addition salts. The invention also relates to the solvates, e.g. hydrates or alcoholates, of these compounds.

The invention accordingly relates to the compounds of the formula I and a process for the preparation of compounds of the formula I, according to Claim 1.

The process for the preparation of compounds of the formula I, (1H-indol-5-yl)-(4-phenethylpiperazin-1-yl) methanone being excluded, is characterized in that
a) a compound of the formula II

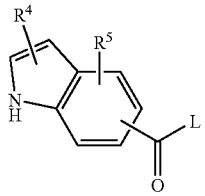

II in which L is Cl, Br, I or a free or reactively functionally modified OH group, and $R^4$ and $R^5$ have the meaning indicated in formula I, is reacted with a compound of the formula III

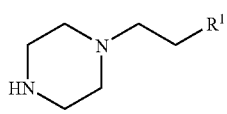

III in which $R^1$ has the meaning indicated in formula I, or
b) a compound of the formula IV

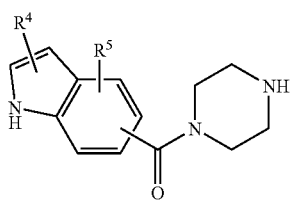

IV in which $R^4$ and $R^5$ have the meaning indicated in formula I, is reacted with a compound of the formula V

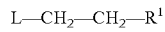

L—CH$_2$—CH$_2$—R$^1$    V in which L is Cl, Br, I or a free or reactively functionally modified OH group, and $R^1$ has the meaning indicated in formula I, or
c) if appropriate, one of the radicals $R^1$, $R^4$ and/or $R^5$ is converted into another radical $R^1$, $R^4$ and/or $R^5$ by cleaving, for example, an OA group with formation of an OH group and/or converting a CHO group into a CN group, and/or a base of the formula I which is obtained is converted into one of its salts by treating with an acid.

The invention also relates to the compounds of the formula I, and to their physiologically acceptable salts and solvates as medicaments, (1H-indol-5-yl)-(4-phenethylpiperazin-1-yl)methanone being excluded The invention relates in particular to the compounds of the formula I, and to their physiologically acceptable salts and solvates as medicaments having 5-HT$_{2A}$ receptor-antagonistic action.

The invention also relates to the compounds of the formula I, and their enantiomers and diastereomers, and their salts.

The indole ring can also be replaced by an isatin unit. Isatin is an isolole which is substituted by oxo in the 2- and 3-position=indole-2,3-dione.

For all radicals which occur a number of times, such as, for example, A or Hal, it holds true that their meanings are independent of one another.

The radical A is alkyl and has 1 to 6, preferably 1, 2, 3 or 4, in particular 1 or 2, C atoms. Alkyl is therefore in particular, for example, methyl, furthermore ethyl, n-propyl, isopropyl, n-butyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methyl-propyl, 1,1,2- or 1,2,2-trimethylpropyl, furthermore trifluoromethyl or pentafluoroethyl.

Acyl preferably has 1–6 C atoms and is, for example, formyl, acetyl, propionyl, butyryl, furthermore trifluoroacetyl or pentafluoropropionyl.

Alkylene is propylene, butylene or pentylene. OA is preferably methoxy, furthermore also ethoxy, n-propoxy, isopropoxy, n-butoxy, isobutoxy, sec-butoxy or tert-butoxy.

Hal is fluorine, chlorine, bromine or iodine, in particular fluorine or chlorine.

$R^1$ is unsubstituted, preferably—as indicated—monosubstituted phenyl or naphthyl, specifically preferably phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-hydroxyphenyl, o-, m- or p-nitrophenyl, o-, m- or p-trifluoromethoxyphenyl, o-, m- or p-cyanophenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-difluoromethoxyphenyl, o-, m- or p-fluoromethoxyphenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl- 6-chloro-, 3-chloro-4-methyl-, 3-chloro-5-methyl- or 3-methyl-4-chlorophenyl, 2-bromo-3-methyl-, 2-bromo-4-methyl-, 2-bromo-5-methyl-, 2-bromo-6-methyl-, 2-methyl-3-bromo-, 2-methyl-4-bromo, 2-methyl-5-bromo-, 2-methyl-6-bromo-, 3-bromo-4-methyl, 3-bromo-5-methyl- or 3-methyl-4-bromophenyl, 2,4- or 2,5-dinitrophenyl, 2,5- or 3,4-dimethoxyphenyl, 3-nitro-4-chlorophenyl, 2,3,4-, 2,3,5-, 2,3,6-, 2,4,6- or 3,4,5-trichlorophenyl, 2,4,6-tri-tert-butylphenyl, furthermore preferably 2-nitro-4-trifluoromethylphenyl, 3,5-ditrifluoromethylphenyl, 2,5-dimethylphenyl, 2-hydroxy-3,5-dichlorophenyl, 2-fluoro-5- or 4-fluoro-3-trifluoromethylphenyl, 4-chloro-2- or 4-chloro-3-trifluoromethyl-, 2-chloro-4- or 2-chloro-5-trifluoromethylphenyl, 4-bromo-2- or 4-bromo-3-trifluoromethylphenyl, p-iodophenyl, 2-nitro-4-methoxyphenyl, 2,5-dimethoxy-4-nitrophenyl, 2-methyl-5-nitrophenyl, 2,4-dimethyl-3-nitrophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 3-bromo-6-methoxyphenyl, 3-chloro-6-methoxyphenyl, 2-methoxy-5-methylphenyl or 2,4,6-triisopropylphenyl.

$R^1$ is also $Het^1$. $Het^1$ is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-; 3-, 4-, 5-, 6 or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzthiazolyl, 2-, 4-, 5-, 6- or 7-benzisothiazolyl, 4-, 5-, 6- or 7-benzo-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl.

$R^1$ is very particularly preferably phenyl, p-chlorophenyl, p-fluorophenyl, thiophen-2-yl, 5-chlorothiophen-2-yl, 2,5-dichlorothiophen-3-yl and 2- or 3-furyl.

$R^4$, $R^5$ are in each case independently of one another preferably H, Hal, alkyl having 1–6 C atoms, alkoxy having 1–6 C atoms or hydroxyl, furthermore cyano or acyl.

$R^4$ is preferably H, Hal, A, OA, OH, CN or acyl. $R^5$ is preferably H.

Preferred compounds of the formula I are those in which the $R^1$—$CH_2$—$CH_2$-piperazinecarbonyl radical substitutes the 4-, 5-, 6- or 7-position of the indole ring.

Accordingly, the invention relates in particular to those compounds of the formula I in which at least one of the radicals mentioned has one of the preferred meanings indicated above. Some preferred groups of compounds can be expressed by the following subformulae Ia to Ii, which correspond to the formula I and in which the radicals not designated in greater detail have the meaning indicated in formula I, but in which in Ia $R^1$ is phenyl;
in Ib $R^1$ is phenyl which is unsubstituted or monosubstituted by Hal;
in Ic $R^1$ is phenyl which is monosubstituted by Hal, or $Het^1$;
in Id $R^1$ is phenyl which is unsubstituted or monosubstituted by Hal, or $Het^1$;

in Ie $R^1$ is phenyl which is unsubstituted or monosubstituted by Hal, or $Het^1$,
$Het^1$ is an unsaturated heterocyclic ring system which is unsubstituted or mono- or disubstituted by Hal or A and contains one or two identical or different heteroatoms such as nitrogen, oxygen and sulfur;
in If $R^1$ is phenyl which is unsubstituted or monosubstituted by Hal, or $Het^1$,
$R^4$ and $R^5$ in each case independently of one another are H, HAL or A,
$Het^1$ is an unsaturated heterocyclic ring system which is unsubstituted or mono- or disubstituted by Hal or A and contains one or two identical or different heteroatoms such as nitrogen, oxygen and sulfur,
in Ig $R^1$ is phenyl which is unsubstituted or monosubstituted by Hal, or $Het^1$,
$R^4$, $R^5$ in each case independently of one another are H, Hal or A,
$R^4$ and $R^5$ together are also alkylene having 3–5 C atoms
$Het^1$ is thienyl or furyl which is unsubstituted or mono- or disubstituted by Hal or A,
in Ih $R^1$ is phenyl which is unsubstituted or monosubstituted by Hal, or $Het^1$,
$R^4$ is H, Hal, CN, acyl or A,
$R^5$ is H,
$R^4$ and $R^5$ together are also alkylene having 3–5 C atoms,
$Het^1$ is thienyl or furyl which is unsubstituted or mono- or disubstituted by Hal or A;
in Ii $R^1$ is phenyl or naphthyl which is unsubstituted or monosubstituted by Hal, or $Het^1$,
$R^4$ is H, Hal, CN, acyl, A or $CONH_2$,
$R^5$ is H,
$R^4$ and $R^5$ together are also alkylene having 3–5 C atoms,
$Het^1$ is thienyl or furyl which is unsubstituted or mono- or disubstituted by Hal or A,
and where the indole ring can also be replaced by an isatin unit.

The compounds of the formula I and also the starting substances for their preparation are otherwise prepared by methods known per se, such as are described in the literature (e.g. in the standard works such as Houben-Weyl, Methoden der Organischen Chemie [Methods of Organic Chemistry], Georg Thieme Verlag, Stuttgart; Organic Reactions, John Wiley & Sons, Inc., New York), namely under reaction conditions such as are known and suitable for the reactions mentioned. Use can also be made in this case of variants which are known per se, but not mentioned here in greater detail.

If desired, the starting substances for the claimed process can also be formed in situ in such a way that they are not isolated from the reaction mixture, but immediately reacted further to give the compounds of the formula I. On the other hand, it is possible to carry out the reaction stepwise.

In the compounds of the formulae II and V, the radical L is preferably Cl or Br; however, it can also be I, OH or otherwise preferably a reactive functionally modified OH group, in particular alkylsulfonyloxy having 1–6 (e.g. methanesulfonyloxy) or arylsulfonyloxy having 6–10 C atoms (e.g. benzenesulfonyloxy, p-toluenesulfonyloxy, 1- or 2-naphthalenesulfonyloxy) or otherwise trichloromethoxy, alkoxy, such as, for example, methoxy, ethoxy, propoxy or butoxy, furthermore also phenoxy.

The compounds of the formula I can preferably be obtained by reacting compounds of the formula II with compounds of the formula III.

As a rule, the starting substances of the formulae II and III are known; the unknown compounds of the formulae II and III can easily be prepared analogously to the known compounds.

The reaction of the compounds II and III proceeds according to methods such as are known from the literature for the alkylation or acylation of amines. However, it is also possible to react the compounds in the presence of an indifferent solvent. Suitable solvents are, for example, hydrocarbons, such as benzene, toluene, xylene; ketones such as acetone, butanone; alcohols such as methanol, ethanol, isopropanol, n-butanol; ethers such as tetrahydrofuran (THF) or dioxane; amides such as dimethylformamide (DMF) or N-methylpyrrolidone; nitrites such as acetonitrile, and, if appropriate, also mixtures of these solvents with one another or mixtures with water. The addition of an acid-binding agent, for example of an alkali metal or alkaline earth metal hydroxide, carbonate or bicarbonate or another salt of a weak acid of the alkali or alkaline earth metals, preferably of potassium, sodium or calcium, or the addition of an organic base such as triethylamine, dimethylaniline, pyridine or quinoline or of an excess of piperazine derivative of the formula II can be favourable. Depending on the conditions used, the reaction time is between a few minutes and 14 days; the reaction temperature between approximately 0 and 150°, normally between 20 and 130°.

In addition, compounds of the formula I can be prepared by reacting amines of the formula IV with a component of the formula V comprising the radical $R^1$.

As a rule, the respective components are known or can be prepared by known processes as already described.

A base of the formula I obtained can be converted into the associated acid addition salt using an acid. For this reaction, suitable acids are those which yield physiologically acceptable salts. Thus inorganic acids can be used, e.g. sulfuric acid, hydrohalic acids such as hydrochloric acid or hydrobromic acid, phosphoric acids such as orthophosphoric acid, nitric acid, sulfamic acid, furthermore organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxy-ethanesulfonic acid, benzenesulfonic acid, p-toluene-sulfonic acid, naphthalenemono- and -disulfonic acids and laurylsulfuric acid.

The free bases of the formula I can, if desired, be liberated from their salts by treatment with strong bases such as sodium or potassium hydroxide, or sodium or potassium carbonate, if no further acidic groups are present in the molecule. In those cases where the compounds of the formula I have free acid groups, salt formation can likewise be achieved by treatment with bases. Suitable bases are alkali metal hydroxides, alkaline earth metal hydroxides or organic bases in the form of primary, secondary or tertiary amines.

The invention furthermore relates to the medicaments according to the invention having 5-$HT_{2A}$ receptor-antagonistic action for the treatment of psychoses, schizophrenia, depression, neurological disorders, memory disorders, Parkinson's disease, amyotrophic lateral sclerosis, Alzheimer's disease, Huntington's disease, eating disorders such as bulimia, nervous anorexia, premenstrual syndrome and/or for positively affecting compulsive behaviour (obsessive-compulsive disorder, OCD).

The invention also relates to a pharmaceutical preparation comprising at least one medicament according to the invention and also, if appropriate, vehicles and/or excipients and, if appropriate, other active compounds.

In this case, the medicaments can be brought into a suitable dose form together with at least one solid, liquid and/or semiliquid vehicle or excipient and, if appropriate, in combination with one or more further active compounds.

The invention furthermore relates to the use of the compounds according to the invention and/or of their physiologically acceptable salts and solvates for the production of a medicament having 5-$HT_{2A}$ receptor-antagonistic action.

The invention also relates to the use of the compounds according to the invention and/or of their physiologically acceptable salts and solvates for the production of a medicament having 5-$HT_{2A}$ receptor-antagonistic action for the treatment of psychoses, schizophrenia, depression, neurological disorders, memory disorders, Parkinson's disease, amyotrophic lateral sclerosis, Alzheimer's disease, Huntington's disease, eating disorders such as bulimia, nervous anorexia, premenstrual syndrome and/or for positively affecting compulsive behaviour (obsessive-compulsive disorder, OCD).

The pharmaceutical preparations can be employed as medicaments in human and veterinary medicine. Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The novel compounds can also be lyophilized and the lyophilisates obtained used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colourants, flavourings and/or aromatizers. They can, if desired, also contain one or more further active compounds, e.g. one or more vitamins.

In this case, the substances according to the invention are as a rule administered in analogy to known preparations, preferably in doses between approximately 0.1 and 500 mg, in particular between 5 and 300 mg, per dose unit. The daily dose is preferably between approximately 0.01 and 250 mg/kg, in particular between 0.02 and 100 mg/kg, of body weight.

In this case, the substances according to the invention as a rule are preferably administered in doses of between approximately 1 and 500 mg, in particular between 5 and 100 mg per dose unit. The daily dose is preferably between approximately 0.02 and 10 mg/kg of body weight. The specific dose for each intended patient depends, however, on all sorts of factors, for example on the efficacy of the specific compound employed, on the age, body weight, general state of health, sex, on the diet, on the time and route of administration, on the excretion rate, pharmaceutical combination and severity of the particular disorder to which the therapy applies. Oral administration is preferred.

Above and below, all temperatures are indicated in ° C. In the examples below, "customary working up" means: if necessary, the solvent is removed, if necessary, water is added, if necessary, the mixture is adjusted, depending on the constitution of the final product, to a pH of between 2 and 10 and extracted with ethyl acetate or dichloromethane, the organic phase is separated off, dried over sodium sulfate, filtered and concentrated, and the residue is purified by chromatography on silica gel and/or by crystallization.

EXAMPLE A1

Preparation of a suspension of 5-HT$_{2A}$ receptors: Frontal rat cortex is homogenized in ice-cold buffer. The homogenate is centrifuged for 10 minutes at 4° C. and 50,000×g. The pellet is resuspended in 2.5 ml of ice-cold tris buffer, made up with 10 ml of additional buffer and centrifuged as described above. The pellet is then resuspended in buffer and diluted to give a homogenate which contains 60 mg of material/ml. 0.1 ml of the suspension, 100 µl of a 5 nM solution of [$^3$H]ketanserin, 100 µl of a solution of the test compound (concentration in the range from $10^{-5}$ to $10^{-10}$ mol per litre) are added to the incubation tubes and made up to 1 ml with buffer. The tubes are incubated for 15 minutes at 37° C. After termination of the incubation by immersing the tubes in an ice bath, the cooled suspension is filtered through a glass filter in vacuo. The filters are washed 3× with 5 ml of cold buffer and then transferred to scintillation tubes. The filters are analysed by means of liquid scintillation spectrometry in 8 ml of Triton X scintillator fluid.

EXAMPLE 1

A solution of 2.0 g of 4-carboxyindole and 8.1 g of 2-chloro-1-methylpyridinium iodide in 60 ml of N-methylpyrrolidone (NMP) is treated with a solution of 2.36 g of 4-phenethylpiperazine and 8.2 g of ethyldi-isopropylamine (EDIPA) in 20 ml of NMP and subsequently stirred at room temperature for 3 hours. The mixture is worked up in the customary manner and the crude product is obtained. This is dissolved in acetone and the hydrochloride is precipitated using aqueous hydrochloric acid. After drying, 4.59 g of (1H-indol-4-yl)-(4-phenethylpiperazin-1-yl)methanone, hydrochloride, m.p. 289.3°, is obtained.

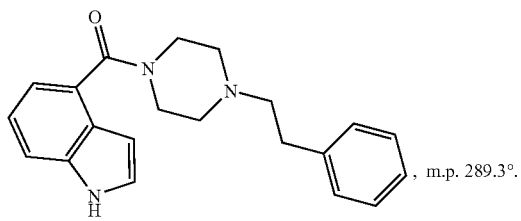, m.p. 289.3°.

The following compounds are obtained analogously
  (1H-indol-4-yl)-[4-(4-fluorophenethyl)piperazin-1-yl]methanone, hydrochloride, m.p. 250°;
  (1H-indol-4-yl)-[4-(thiophen-2-ylethyl)piperazin-1-yl]methanone, (1H-indol-4-yl)-[4-(5-chlorothiophen-2-ylethyl)piperazin-1-yl]methanone, (1H-indol-4-yl)-[4-(thiophen-3-ylethyl)piperazin-1-yl]methanone, (1H-indol-4-yl)-[4-(2,5-dichlorothiophen-3-ylethyl)piperazin-1-yl]methanone, hydrochloride, m.p. 166–168°;
  (1H-indol-5-yl)-[4-(4-fluorophenethyl)piperazin-1-yl]methanone, (1H-indol-5-yl)-[4-(thiophen-2-ylethyl)piperazin-1-yl]methanone, (1H-indol-5-yl)-[4-(5-chlorothiophen-2-ylethyl)piperazin-1-yl]methanone, (1H-indol-5-yl)-[4-(thiophen-3-ylethyl)piperazin-1-yl]methanone, (1H-indol-5-yl)-[4-(2,5-dichlorothiophen-3-ylethyl)piperazin-1-yl]methanone, (3-formyl-1H-indol-5-yl)-[4-(4-fluorophenethyl)piperazin-1-yl]methanone, hydrochloride, m.p. 240.9°;
  (1H-indol-6-yl)-[4-phenethylpiperazin-1-yl]methanone,
  (1 H-indol-6-yl)-[4-(4-fluorophenethyl)piperazin-1-yl]methanone, hydrochloride, m.p. 284.0–284.4°;
  (1H-indol-6-yl)-[4-(thiophen-2-ylethyl)piperazin-1-yl]methanone, hydrochloride, m.p. 204.2–205.7°;
  (1H-indol-6-yl)-[4-(5-chlorothiophen-2-ylethyl)piperazin-1-yl]methanone, hydrochloride, m.p. 251.0–252.5°;
  (1H-indol-6-yl)-[4-(thiophen-3-ylethyl)piperazin-1-yl]methanone, (1H-indol-6-yl)-[4-(2,5-dichlorothiophen-3-ylethyl)piperazin-1-yl]methanone, hydrochloride, m.p. 240–241°;
  (3-formyl-(1H-indol-6-yl)-[4-(4-fluorophenethyl)piperazin-1-yl]methanone, (3-cyano-1H-indol-6-yl)-[4-(4-fluorophenethyl)piperazin-1-yl]methanone, hydrochloride, m.p. 280°;
  (1H-indol-7-yl)-(4-phenethylpiperazin-1-yl)methanone, hydrochloride, m.p. 221°;
  (1H-indol-7-yl)-[4-(4-fluorophenethyl)piperazin-1-yl]methanone, hydrochloride, m.p. 274°;
  (1H-indol-7-yl)-[4-(thiophen-2-ylethyl)piperazin-1-yl]methanone, (1H-indol-7-yl)-[4-(5-chlorothiophen-2-ylethyl) piperazin-1-yl]methanone, hydrochloride, m.p. 251.0–252.5°;
  (1H-indol-7-yl)-[4-(thiophen-3-ylethyl)piperazin-1-yl]methanone, (1H-indol-7-yl)-[4-(2,5-dichlorothiophen-3-ylethyl)piperazin-1-yl]methanone, (3-formyl-1H-indol-7-yl)-[4-(4-fluorophenethyl)piperazin-1-yl]methanone, hydrochloride, m.p. 287°;
  (3-cyano-1H-indol-7-yl)-[4-(4-fluorophenethyl)piperazin-1-yl]methanone, hydrochloride, m.p. >300°;
  (2,3-dimethyl-1H-indol-7-yl)-(4-phenethylpiperazin-1-yl)methanone, (2,3-dimethyl-1H-indol-7-yl)-[4-(4-fluorophenethyl)piperazin-1-yl]methanone, 86.5–89°;
  (2,3-dimethyl-1H-indol-7-yl)-[4-(thiophen-2-ylethyl)piperazin-1-yl]methanone, (2,3-dimethyl-1H-indol-7-yl)-[4-(5-chlorothiophen-2-ylethyl)piperazin-1-yl]methanone, (2,3-dimethyl-1H-indol-7-yl)-[4-(thiophen-3-ylethyl)piperazin-1-yl]methanone, (2,3-dimethyl-1H-indol-7-yl)-[4-(2,5-dichlorothiophen-3-ylethyl)piperazin-1-yl]methanone, (6,7,8,9-tetrahydro-5H-carbazol-3-yl)-(4-phenethylpiperazin-1-yl)methanone, hydrochloride, m.p. 235–237°; (6,7,8,9-tetrahydro-5H-carbazol-3-yl)-[4-(4-fluorophenethyl) piperazin-1-yl]methanone, (6,7,8,9-tetrahydro-5H-carbazol-3-yl)-[4-(thiophen-2-ylethyl)piperazin-1-yl]methanone, (6,7,8,9-tetrahydro-5H-carbazol-3-yl)-[4-(5-chlorothiophen-2-ylethyl)piperazin-1-yl]methanone, (6,7,8,9-tetrahydro-5H-carbazol-3-yl)-[4-(thiophen-3-ylethyl)piperazin-1-yl]methanone, (6,7,8,9-tetrahydro-5H-carbazol-3-yl)-[4-(2,5-dichlorothiophen-3-ylethyl)piperazin- 1-yl]methanone.
  (3-formyl-1H-indol-6-yl)-[4-(4-fluorophenethyl)piperazin-1-yl]methanone, hydrochloride, m.p. 279.3°;
  (1H-indol-6-yl)-[4-(5-chlorothiophen-2-ylethyl)piperazin-1-yl]methanone, hydrochloride, m.p. 257.5–259.0°;
  (1H-indol-4-yl)-[4-(5-chlorothiophen-2-ylethyl)piperazin-1-yl]methanone, hydrochloride, m.p. 266–267°;
  (3-cyano-1H-indol-5-yl)-[4-(4-fluorophenethyl)piperazin-1-yl]methanone, hydrochloride, m.p. 210°;

(3-cyano-1H-indol-7-yl)-[4-(naphth-2-ylethyl)piperazin-1-yl]methanone, hydrochloride, m.p. 284.0–285.5°;

(3-cyano-1H-indol-4-yl)-[4-(4-fluorophenethyl)piperazin-1-yl]methanone, hydrochloride, m.p. 284.0–285.5°;

(3-cyano-1H-indol-4-yl)-[4-(2-fluorophenethyl)piperazin-1-yl]methanone, hydrochloride, m.p. 213–215.5°;

(3-cyano-IH-indol-7-yl)-[4-(2-fluorophenethyl)piperazin-1-yl]methanone, hydrochloride, m.p. 212.5–214°;

(3-aminocarbonyl-1H-indol-7-yl)-[4-(4-fluorophenethyl)piperazin-1-yl]methanone, hydrochloride, m.p. 280–281°;

(3-cyano-1H-indol-7-yl)-[4-(4-fluorophenethyl)piperazin-1-yl]methanone, methanesulfonate, m.p. 212.5–214°;

(3-cyano-1H-indol-7-yl)-[4-(5-chlorothiophen-2-ylethyl)piperazin-1-yl]methanone, hydrochloride, m.p. 301.5–303.0°;

(3-cyano-1H-indol-7-yl)-(4-phenethyl-piperazin-1-yl)methanone, methanesulfonate, m.p. 294.7–297°;

(3-cyano-1H-indol-7-yl)-[4-(2,4-difluorophenethyl)piperazin-1-yl]methanone, hydrochloride, m.p. 295.6–297.0°;

7-{4-[2-(4-fluorophenyl)ethyl]piperazin-1-carbonyl}-1H-indole-2,3-dione.

The following examples relate to pharmaceutical preparations:

EXAMPLE A

Injection Vials

A solution of 100 g of an active compound of the formula I and 5 g of disodium hydrogen phosphate in 3 l of double-distilled water is adjusted to pH 6.5 using 2 N hydrochloric acid, sterile-filtered, filled into injection vials, lyophilized and aseptically sealed. Each injection vial contains 5 mg of active compound.

EXAMPLE B

Suppositories

A mixture of 20 g of an active compound of the formula I is fused with 100 g of soya lecithin and 1400 g of cocoa butter, poured into moulds and allowed to cool. Each suppository contains 20 mg of active compound.

EXAMPLE C

Solution

A solution is prepared from 1 g of an active compound of the formula I, 9.38 g of $NaH_2PO_4 \times 2$ $H_2O$, 28.48 g of $NaH_2PO_4 \times 12$ $H_2O$ and 0.1 g of benzalkonium chloride in 940 ml of double-distilled water. It is adjusted to pH 6.8, made up to 1 l and sterilized by irradiation. This solution can be used in the form of eye drops.

EXAMPLE D

Ointment 500 mg of an active compound of the formula I are mixed with 99.5 g of petroleum jelly under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

EXAMPLE F

Coated Tablets

Analogously to Example E, tablets are pressed and are then coated in a customary manner with a coating of sucrose, potato starch, talc, tragacanth and colorant.

EXAMPLE G

Capsules 2 kg of active compound of the formula I are filled into hard gelatin capsules in a customary manner such that each capsule contains 20 mg of the active compound.

EXAMPLE H

Ampoules

A solution of 1 kg of active compound of the formula I in 60 l of double-distilled water is filled into ampoules, lyophilized under aseptic conditions and aseptically sealed. Each ampoule contains 10 mg of active compound.

What is claimed is:

1. A compound according to formula IV

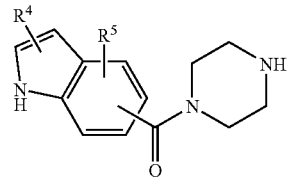

IV wherein $R^4$ and $R^5$ are each, independently, H, CN, acyl, Hal, A, OA, OH, $CONH_2$, CONHA or $CONA_2$, $R^4$ and $R^5$ together are alternatively alkylene having 3–5 carbon atoms, A is alkyl having 1–6 carbon atoms, Hal is F, Cl, Br or I, and where the indole ring may be replaced by an isatin unit, or a physiologically acceptable salt or solvate thereof.

2. A compound according to claim 1, wherein $R^4$ and $R^5$ are each, independently, H, CN, acyl having 1–6 C atoms, Hal, A, OA or OH.

3. A compound according to claim 1, wherein $R^5$ is H and $R^4$ is H, Hal, A, OA, OH, CN or acyl having 1–6 C atoms.

4. A compound according to claim 1, wherein $R^4$ and $R^5$ are, in each case independently, H, CN, formyl, acetyl, propionyl, butyryl, trifluoroacetyl, Hal, A, OA, OH, $CONH_2$, CONHA or $CONA_2$.

5. A compound according to claim 1, wherein $R^5$ is H and $R^4$ is H, CN, formyl, acetyl, propionyl, butyryl, trifluoroacetyl, Hal, A, OA, OH, $CONH_2$, CONHA or $CONA_2$.

6. A compound according to claim 1, wherein $R^4$ and $R^5$ are, in each case independently, H, Hal, alkyl having 1–6 C atoms, alkoxy having 1–6 C atoms, hydroxyl, cyano or acyl having 1–6 C atoms.

7. A compound according to claim 1, wherein $R^4$ and $R^5$ are, in each case independently, H, Hal, or alkyl having 1–6 C atoms.

8. A compound according to claim 1, wherein $R^4$ and $R^5$ are, in each case independently, H, Hal, or alkyl having 1–6 C atoms, or $R^4 R^5$ together are alkylene having 3–5 C atoms.

9. A compound according to claim a 1, wherein $R^5$ H and $R^4$ is H, Hal, CN, acyl having 1–6 C atoms or alkyl having 1–6 C atoms, or $R^4$ and $R^5$ together are alkylene having 3–5 C atoms.

10. A compound according to claim 1, wherein $R^5$ is H and $R^4$ is H, Hal, CN, acyl having 1–6 C atoms, $CONH_2$, or alkyl having 1–6 C atoms, or $R^4$ and $R^5$ together are alkylene having 3–5 C atoms.

11. A compound according to claim 1, wherein said compound is in the form of a hydrate or an alcoholate.

12. A compound according to claim 1, wherein said compound is in the form of a physiologically acceptable salt.

13. A physiologically acceptable salt of the compound (3-cyano-1H-indol-7-yl)[4-(4-fluorophenethyl)piperazin-1-yl]-methanone wherein said salt is an acid addition salt obtained from an acid selected from sulfuric acid, hydrohalic acids, phosphoric acids, nitric acid, sulfamic acid, and aliphatic, alicyclic, araliphatic, aromatic or heterocyclic mono- or polybasic carboxylic, sulfonic or sulfuric acids.

14. A physiologically acceptable salt according to claim 13, wherein said acid is selected from sulfuric acid, hydrochloric acid, hydrobromic acid, orthophosphoric acid, nitric acid, sulfamic acid, formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulfonic acid, ethanesulfonic acid, ethanedisulfonic acid, 2-hydroxyethanesulfonic acid, benzenesulfonic acid, p-toluenesulfonic acid, naphthalenemonosulfonic acid, naphthalenedisulfomc acid and laurylsulfuric acid.

15. A physiologically acceptable salt according to claim 13, wherein said acid is selected from formic acid, acetic acid, propionic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, and isonicotinic acid.

16. A physiologically acceptable salt according to claim 13, wherein said acid is selected from malonic acid, succinic acid, pimelic acid, fumaric acid, and maleic acid.

17. A physiologically acceptable salt according to claim 13, wherein said acid is selected from sulfuric acid, hydrochloric acid, hydrobromic acid, orthophosphoric acid, succinic acid, fumaric acid, and maleic acid.

18. A compound selected from:
(1H-indol-4-yl)-[4-(thiophen-2-ylethyl)piperazin-1-yl] methanone;
(1H-indol-4-yl)-[4-(5-chlorothiophen-2-ylethyl)piperazin-1-yl]methanone;
(1H-indol-4-yl)-[4-(thiophen-3-ylethyl)piperazin-1-yl] methanone;
(1H-indol-4-yl)-[4-(2,5-dichlorothiophen-3-ylethyl)piperazin-1-yl]methanone;
(1H-indol-5-yl)-[4-(thiophen-2-ylethyl)piperazin-1-yl] methanone;
(1H-indol-5-yl)-[4-(thiophen-3-ylethyl)piperazin-1-yl] methanone;
(1H-indol-5-yl)-[4(2,5-dichlorothiophen-3-ylethyl)piperazin-1-yl]methanone;
(1H-indol-6-yl)-[4-(thiophen-2-ylethyl)piperazin-1-yl] methanone;
(1H-indol-6-yl)-[4-(5-chlorothiophen-2ylethyl)piperazin-1-yl]methanone;
(1H-indol-6-yl)-[4-(thiophen-3-ylethyl)piperazin-1-yl] methanone;
(1H-indol-6-yl)-[4-(2,5-dichlorothiophen-3-ylethyl)piperazin-1-yl]methanone;
(1H-indol-7-yl)[4-(thiophen-2-ylethyl)piperazin-1-yl] methanone;
(1H-indol-7-yl)-[4-(5-chlorothiophen-2-ylethyl)piperazin-1-yl]methanone;
(1H-indol-7-yl)-[4-(thiophen-3-ylethyl)piperazin- 1 -yl] methanone;
(1H-indol-7-yl)-[4-(2,5-dichlorothiophen-3-ylethyl)piperazin-1-yl]methanone;
(2,3-dimethyl-1H-indol-7-yl)-[4-(thiophen-2-ylethylethyl)piperazin-1-yl]methanone;
(2,3-dimethyl-1H-indol-7-yl)-[4-(5-chlorothiophen-2-yl) piperazin-1-yl]methanone;
(2,3-dimethyl-1H-indol-7-yl)-[4-(thiophen-3-ylethyl)piperazin-1-yl]methanone;
(2,3-dimethyl-1H-indol-7-yl)-[4-(2,5-dichlorothiophen-3-ylethyl)piperazin-1-yl]methanone;
(6,7,8,9-tetrahydro-5H-carbazol-3-yl)-[4-(thiophen-2-ylethyl)piperazin-1-yl]methanone;
(6,7,8,9-tetrahydro-5H-carbazol-3-yl)-[4-(5-chlorothiophen-2-ylethyl)piperazin -1-yl]methanone;
(6,7,8,9-tetrahydro-5H-carbazol-3-yl)-[4-(thiophen-3-ylethyl)piperazin-1-yl]methanone;
(6,7,8,9-tetrahydro-5H-carbazol-3-yl)-[4-(2,5-dichlorothiophen-3-ylethyl)piperazin -1-yl]methanone; and
physiologically acceptable salts and solvates thereof.

19. A compound according to claim 18, wherein said compound is
(1H-indol-4-yl)-[42,5-dichlorothiophen-3-yl)piperazin-1-yl]methanone, hydrochloride;
(1H-indol-6-yl)-[4-thiophen-2-yl)piperazin-1-yl]methanone, hydrochloride;
(1H-indol-6-yl)-[4-(5-chlorothiophen-2-yl)piperazin-1-yl]methanone, hydrochloride;
(1H-indol-6-yl)-[4-(2,5-dichlorothiophen-3-yl)piperazin-1-yl]methanone, hydrochloride; or
(1H-indol-7-yl)-[4-(5-chlorothiophen-2-yl)piperazin-1-yl]methanone, hydrochloride.

20. A compound according to claim 18, wherein said compound is selected from:
(1H-indol-4-yl)-[4-(thiophen-2-yl)piperazin-1-yl]methanone;
(1H-indol-4-yl)-[4-(5-chlorothiophen-2-yl)piperazin-1-yl]methanone;
(1H-indol-4-yl)-[4-(thiophen-3-yl)piperazin-1-yl]methanone;
(1H-indol-4-yl)-[4-(2,5-dichlorothiophen-3-yl)piperazin-1-yl]methanone;
(1H-indol-5-yl)-[4-(thiophen-2-yl)piperazin-1-yl]methanone;
(1H-indol-5-yl)-[4-(5-chlorothiophen-2-yl)piperazin-1-yl]methanone;
(1H-indol-5-yl)-[4-(thiophen-3-yl]piperazin-1-yl methanone;
(1H-indol-5-yl)-[4-(2,5-dichlorothiophen-3-yl)piperazin-1-yl]methanone;
(1H-indol-6-yl)-[4-(thiophen-2-y1)piperazin-1-yl]methanone;
(1H-indol-6-yl)-[4-(5-chlorothiophen-2-yl)piperazin-1-yl]methanone;

(1H-indol-6-yl)-[4-(thiophen-3-yl)piperazin-1-yl]methanone;
(1H-indol-6-yl)-[4-(2,5-dichlorothiophen-3-yl)piperazin-1-yl]methanone;
(1H-indol-7-yl)-[4-(thiophen-2-yl)piperazin-1-yl]methanone;
(1H-indol-7-yl)-[4-(5-chlorothiophen-2-yl)piperazin-1-yl]methanone;
(1H-indol-7-yl)-[4-(thiophen-3-yl)piperazin-1-yl]methanone;
(1H-indol-7-yl)-[4-(2,5-dichlorothiophen-3-yl)piperazin-1-yl]methanone; and
physiologically acceptable salts and solvates thereof.

21. A compound selected from:
(1H-indol-6-yl)-[4-(5-chlorothiophen-2-yl)piperazin-1-yl]methanone;
(1H-indolyl)-[4-(5-chlorothiophen-2-yl)piperazin-1-yl]methanone;
(3-cyano-1H-indol-7-yl)-[4-(5-chlorothiophen-2-yl)piperazin-1-yl]methanone; and
physiologically acceptable salts and solvates thereof.

22. A compound according to claim 21, wherein said compound is selected from:
(1H-indol-6-yl)-[4-(5-chlorothiophen-2-yl)piperazin-1-yl]methanone, hydrochloride;
(1H-indol-4-yl)-[4-(5-chlorothiophen-2-yl)piperazin-1-yl]methanone, hydrochloride; and
(3-cyano-1H-indol-7-yl)-[4-(5-chlorothiophen-2-yl)piperazin-1-yl]methanone, hydrochloride.

23. A compound selected from:
(1H-indol-4-yl)-(4-phenethylpiperazin-1-yl)methanone;
(1H-indol-4-yl)-[4-(4-fluorophenethyl)piperazin-1-yl]methanone;
(1H-indol-5-yl)-[4-(4-fluorophenethyl)piperazin-1-yl]methanone;
(3-formyl-1H-indol-5-yl)-[4-(4-fluorophenethyl)piperazin-1-yl]methanone;
(1H-indol-6-yl)-[4-phenethylpiperazin-1-yl]methanone;
(1H-indol-6-yl)-[4-(4-fluorophenethyl)piperazin-1-yl]methanone;
(3-formyl-1H-indol-6-yl)-[4-(4-fluorophenethyl)piperazin-1-yl]methanone;
(3-cyano-1H-indol-6-yl)[4-(4-fluorophenethyl)piperazin-1-yl]methanone;
(1H-indol-7-yl)-(4-phenethylpiperazin-1-yl)methanone;
(1H-indol-7-yl)-[4(4-fluorophenethyl)piperazin-1-yl]methanone;
(3-formyl-1H-indol-7-yl)-[4-(4-fluorophenethyl)piperazin-1-yl]methanone;
(3-cyano-1H-indol-7-yl)-[4-(4-fluorophenethyl)piperazin-1-yl]methanone;
(2,3-dimethyl-1H-indol-7-yl)-(4-phenethylpiperazin-1-yl)methanone,
(2,3-dimethyl-1H-indol-7-yl)-[4-(4-fluorophenethyl)piperazin-1-yl]methanone;
(6,7,8,9-tetrahydro-5H-carbazol-3-yl)-(4-phenethylpiperazin-1-yl)methanone;
(6,7,8,9-tetrahydro-5H-carbazol-3-yl)-[4-(4-fluorophenethyl)piperazin-1-yl]methanone; and
physiologically acceptable salts and solvates thereof.

24. A compound according to claim 23, wherein said compound is
(1H-indol-4-yl)-(4-phenethylpiperazin-1-yl)methanone, hydrochloride;
(1H-indol-4-yl)-[4-(4-fluorophenethyl)piperazin-1-yl]methanone, hydrochloride;
(3-formyl-1H-indol-5-yl)-[4-(4-fluorophenethyl)piperazin-1-yl]methanone, hydrochloride;
(1H-indol-6-yl)-[4-(4-fluorophenethyl)piperazin-1-yl]methanone, hydrochloride;
(3-cyano-1H-indol-6-yl)-[4-(4-fluorophenethyl)piperazin-1-yl]methanone, hydrochloride;
(1H-indol-7-yl)-(4-phenethylpiperazin-1-yl)methanone, hydrochloride;
(1H-indol-7-yl)-[4-(4-fluorophenethyl)piperazin-1-yl]methanone, hydrochloride;
(3-formyl-1H-indol-7-yl)-[4-(4-fluorophenethyl)piperazin-1-yl]methanone, hydrochloride;
(3-cyano-1H-indol-7-yl)-[4-(4-fluorophenethyl)piperazin-1-yl]methanone, hydrochloride; or
(6,7,8,9-tetrahydro-5H-carbazol-3-yl)-(4-phenethylpiperazin-1-yl)methanone, hydrochloride.

25. A compound according to claim 23, wherein said compound is selected from:
(1H-indol-4-yl)-(4-phenethylpiperazin-1-yl)methanone;
(1H-indol-4-yl)-[4-(4-fluorophenethyl)piperazin-1-yl]methanone;
(1H-indol-5-yl)-[4-(4-fluorophenethyl)piperazin-1-yl]methanone;
(3-formyl-5-I)-yl)-[4-(4-fluorophenethyl)piperazin-1-yl]methanone;
(1H-indol-6-yl)-[4-phenethylpiperazin-1-yl]methanone;
(1H-indol-6-yl)-[4-(4-fluorophenethyl)piperazin-1-yl]methanone;
(3-formyl-indol-6-yl)-[4-(yl)-[4(4-fluorophenethyl)piperazin-1-yl]methanone;
(3-cyano-1H-indol-6-yl)-[4-(4-fluorophenethyl)piperazin-1-yl]methanone;
(1H-indol-7-yl)-(4-phenethylpiperazin-1-yl)methanone;
(1H-indol-7-yl)-[(4-fluorophenethyl)piperazin-1-yl]methanone;
(3-formyl-1H-indol-7-yl)-[4-(4-fluorophenethyl)piperazin-1-yl]methanone;
(3-cyano-1H-indol-7-yl)-[4-(4-fluorophenethyl)piperazin-1-yl]methanone; and
physiologically acceptable salts and solvates thereof.

26. A compound selected from:
(3-formyl-(1H-indol-6-yl)-[4-(4-fluorophenethyl)piperazin-1-yl]methanone;
(3-cyano-1H-indol-5-yl)-[44-fluorophenethyl)piperazin-1-yl]methanone;
(3-cyano-1 H-indol-7-yl)-[4-(naphtha-2-ylethyl)piperazin-1-yl]methanone;
(3-cyano-1H-indol-4-yl)-[4-(4-fluorophenethyl)piperazin-1-yl]methanone;
(3-cyano-1H-indol-4-yl)-[4-(2-fluorophenethyl)piperazin-1-yl]methanone;
(3-cyano-1H-indol-7-yl)-[4-(2-fluorophenethyl)piperazin-1-yl]methanone;
(3-aminocarbonyl-1H-indol-7-yl)-[4-(4-fluorophenethyl)piperazin-1-yl]methanone;
(3-cyano-1H-indol-7-yl)-[4-(4-fluorophenethyl)piperazin-1-yl]methanone;
(3-cyano-1H-indol-7-yl-(4-phenethyl-piperazin-1-yl)methanone;
(3-cyano-1H-indol-7-yl)-(4-(2,4-difluorophenethyl)piperazin-1-yl]methanone;
7-{4-[2-(4-fluorophenyl) ethyl]piperazin-1-carbonyl}-1H-indole-2,3-dione; and
physiologically acceptable salts and solvates thereof.

27. A compound according to claim 26, wherein said compound is selected from:

(3-formyl-(1H-indol-6-yl)-[4-(4-fluorophenethyl)piperazin-1-yl]methanone, hydrochloride;
(3-cyano-1H-indol-5-yl)-[4-(4-fluorophenethyl)piperazin-1-yl]methanone, hydrochloride;
(3-cyano-1H-indol-7-yl)-[4-(naphtha-2-ylethyl)piperazin-1-yl]methanone, hydrochloride;
(3-cyano-1H-indol-4-yl)-[4-(4-fluorophenethyl)piperazin-1-yl]methanone, hydrochloride;
(3-cyano-1H-indol-4-yl)-[4-(2-fluorophenethyl)piperazin-1-yl]methanone, hydrochloride;
(3-cyano-1H-indol-7-yl)-[4-(2-fluorophenethyl)piperazin-1-yl]methanone, hydrochloride;
(3-aminocarbonyl-1H-indol-7-yl)-[4-(4-fluorophenethyl)piperazin-1-yl]methanone, hydrochloride;
(3-cyano-1H-indol-7-yl)-[4-(4-fluorophenethyl)piperazin-1-yl]methanone, methanesulfonate;
(3-cyano-1H-indol-7-yl-(4-phenethyl-piperazin-1-yl)methanone, hydrochloride; and
(3-cyano-1H-indol-7-yl)-[4-(2,4-di fluorophenethyl)piperazin-1-yl]methanone, hydrochloride.

* * * * *

UNITED STATES PATENT AND TRADEMARK OFFICE
CERTIFICATE OF CORRECTION

PATENT NO. : 7,084,143 B2
APPLICATION NO. : 11/013908
DATED : August 1, 2006
INVENTOR(S) : Gerd Bartoszyk It is certified that error appears in the above-identified patent and that said Letters Patent is hereby corrected as shown below:

Column 13, line 6 reads "C atoms, or $R^4R^5$ together are alkylene having 3-5 C atoms"

should read -- C atoms, or $R^4$ and $R^5$ together are alkylene having 3-5 C atoms --

Column 13, line 7 reads "A compound according to claim a 1, wherein $R^5$ H and"

should read -- A compound according to claim 1, wherein $R^5$ is H and --

Column 13, line 38 reads "naphthalenedisulfomc acid and laurylsulfuric acid" should read -- naphthalenedisulfonic acid and laurylsulfuric acid --

Column 13, line 63 insert

-- (1H-indol-5-yl)-[4-(5-chlorothiophen-2-ylethyl)piperazin-1-yl]methanone; --

Column 13, line 66 reads "(1H-indol-5-yl)-[4(2,5-dichlorothiophen-2-ylethyl)piper-"

should read -- (1H-indol-5-yl)-[4-(2,5-dichlorothiophen-2-ylethyl)piper- --

Column 14, line 3 reads "(1H-indol-6-yl)-[4-(5-chlorothiophen-2ylethyl)piperazin-"

should read -- (1H-indol-6-yl)-[4-(5-chlorothiophen-2-ylethyl)piperazin --

Column 14, lines 17-18 read

"(2,3-dimethyl-1H-indol-7-yl)-[4-(thiophen-2-ylethyl-ethyl"

should read -- 2,3-dimethyl-1H-indol-7-yl)-[4-(thiophen-2-ylethyl --

Column 14, line 19 reads "(2,3-dimethyl-1H-indol-7-yl)-[4-(5-chlorothiophen-2-yl-"

should read -- (2,3-dimethyl-1H-indol-7-yl)-[4-(5-chlorothiophen-2-ylethyl --

Column 14, line 36 reads "(1H-indol-4-yl)-[42,5-dichlorothiophen-3-yl)piperazin-1-"

should read -- (1H-indol-4-yl)-[4-(2,5-dichlorothiophen-3-yl)piperazin-1- --

Column 14, delete lines 58 -59

Column 14, line 60 reads "(1H-indol-5-yl)-[4-(thiophen-3-yl]piperazin-1-yl metha-;"

should read -- (1H-indol-5-yl)-4-(thiophen-3-yl)piperazin-1-yl] metha-; --

UNITED STATES PATENT AND TRADEMARK OFFICE
CERTIFICATE OF CORRECTION

PATENT NO. : 7,084,143 B2
APPLICATION NO. : 11/013908
DATED : August 1, 2006
INVENTOR(S) : Gerd Bartoszyk It is certified that error appears in the above-identified patent and that said Letters Patent is hereby corrected as shown below:

Column 15, line 17 reads "(1H-indolyl)-[4-(5-chlorothiophen-2-yl)piperazin-1-yl]"

should read -- (1H-indolyl)-[4-(5-chlorothiophen-2-yl)piperazin-1-yl] --

Column 15, line 46 reads "(1H-indol-7-yl)-[4(4-fluorophenethyl)piperazin-1-yl]" should read -- (1H-indol-7-yl)-[4-(4-fluorophenethyl)piperazin-1-yl] --

Column 16, line 25 reads "(3-formyl-5-I)-yl)-[4-(4-fluorophenethyl)piperazin-1-yl]"

should read -- (3-formyl-1H-indol-5-yl)-[4-(4-fluorophenethyl)piperazin-1-yl] --

Column 16, line 30 reads "(3-formyl-indol-6-yl)-[4-(yl)-[4(4-fluorophenethyl)piper-"

should read -- (3-formyl-indol-6-yl)-[4-(yl)-[4-(4-fluorophenethyl)piper- --

Column 16, line 36 reads "(1H-indol-7-yl)-[(4-fluorophenethyl)piperazin-1-yl]" should read -- (1H-indol-7-yl)-[4-(4-fluorophenethyl)piperazin-1-yl] --

Column 16, line 44 reads "(3-formyl-(1H-indol-6-yl)-[4-(4-fluorophenethyl)piper-"

should read -- (3-formyl-1H-indol-6-yl)-[4-(4-fluorophenethyl)piper- --

Column 16, line 46 reads "(3-cyano-1H-indol-5-yl)-[44-fluorophenethyl)piperazin-"

should read -- (3-cyano-1H-indol-5-yl)-[4-(4-fluorophenethyl)piperazin- --

Column 16, line 60 reads "(3-cyano-1H-indol-7-yl-(4-phenethyl-piperazin-1-yl)" should read -- (3-cyano-1H-indol-7-yl)-(4-phenethyl-piperazin-1-yl) --

Column 16, line 62 reads "(3-cyano-1H-indol-7-yl)-(4-(2,4-difluorophenethyl)pip-"

should read -- (3-cyano-1H-indol-7-yl)-[4-(2,4-difluorophenethyl)pip- --

Column 17, line 3 reads "(3-formyl-(1H-indol-6-yl)-[4-(4-fluorophenethyl)piper-" should read -- (3-formyl-(-1H-indol-6-yl)-[4-(4-fluorophenethyl)piper- --

UNITED STATES PATENT AND TRADEMARK OFFICE
CERTIFICATE OF CORRECTION

PATENT NO.        : 7,084,143 B2
APPLICATION NO. : 11/013908
DATED             : August 1, 2006
INVENTOR(S)       : Gerd Bartoszyk It is certified that error appears in the above-identified patent and that said Letters Patent is hereby corrected as shown below:

Column 18, line 7 reads "(3-cyano-1H-indol-7-yl-(4-phenethyl-piperazin-1-yl)" should read -- (3-cyano-1H-indol-7-yl)-(4-phenethyl-piperazin-1-yl)" --

Signed and Sealed this

Third Day of November, 2009

David J. Kappos
*Director of the United States Patent and Trademark Office*